United States Patent
De Nijs et al.

(10) Patent No.: US 6,333,450 B1
(45) Date of Patent: Dec. 25, 2001

(54) METHODS OF SELECTING PLANTS HAVING DELAYED OR INHIBITED RIPENING OR SENESCENCE

(75) Inventors: Johannes Jacobus Maria De Nijs; Jacobus Broer, both of Enkhuizen; Johannes Elizabert Van Doorn, Grootebroek, all of (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/358,244

(22) Filed: Jul. 21, 1999

Related U.S. Application Data

(63) Continuation of application No. 08/809,566, filed as application No. PCT/EP95/03811 on Sep. 25, 1995, now abandoned.

(30) Foreign Application Priority Data

Sep. 26, 1994 (GB) .................................................. 9419346
Sep. 26, 1994 (GB) .................................................. 9419348

(51) Int. Cl.⁷ ............................... A01H 5/00; A01H 5/10
(52) U.S. Cl. ........................... 800/306; 800/295; 800/298
(58) Field of Search ............................... 47/58.1, DIG. 1; 435/418, 420; 800/298, 306, 309, 317.1, 317.4, 295

(56) References Cited

FOREIGN PATENT DOCUMENTS

WO 91/01375    2/1991   (WO).
WO 91/09112    6/1991   (WO).
WO 92/02622    2/1992   (WO).

OTHER PUBLICATIONS

Plant Physiology, Third Edition; F.B. Salisbury and C.W. Ross, authors;Wadsworth Publishing Co., Inc., Belmont CA 1985. pp. 348–349.*
Salisbury et al., Plant Physiology, Wadsworth Publishing, Inc., Belmont, CA, pp. 348–349 (1985).
Herner et al., Plant Physiology, 52: 38–42, (1973).
Hobson, J. Sci. Food Agric., 31: 578–584 (1980).
Sandoz Ltd. et al., International Search Report, PCT/EP95/03811, 24 pages, Sep. 25, 1995.
Hamilton et al., Nature, 346: 284–287 (1990).
Kendall et al., HortScience, 23(4): 759–761 (1988).
Kendall et al., HortScience, 16(3): 461, Sect. 2, (1981).

\* cited by examiner

*Primary Examiner*—Amy J. Nelson
*Assistant Examiner*—David H Kruse
(74) *Attorney, Agent, or Firm*—Bruce Vrana

(57) ABSTRACT

The present invention provides, inter alia, a method of obtaining plants which exhibit delayed or inhibited fruit ripening and/or vegetable tissue senescence comprising:

(i) growing seedlings thereof in the presence of an auxin polar transport inhibitor and selecting those seedlings the hypocotyledon of which grows at an acute angle of less than about 70° to the horizontal; and/or—

(ii) contacting the seeds of plants which have a low or reduced polar auxin transport with a conjugation inhibitory amount of an inhibitor of cytokinin-$N^{7,9}$glycosyl conjugation and selecting from the thus contacted seeds those which germinate.

7 Claims, 1 Drawing Sheet

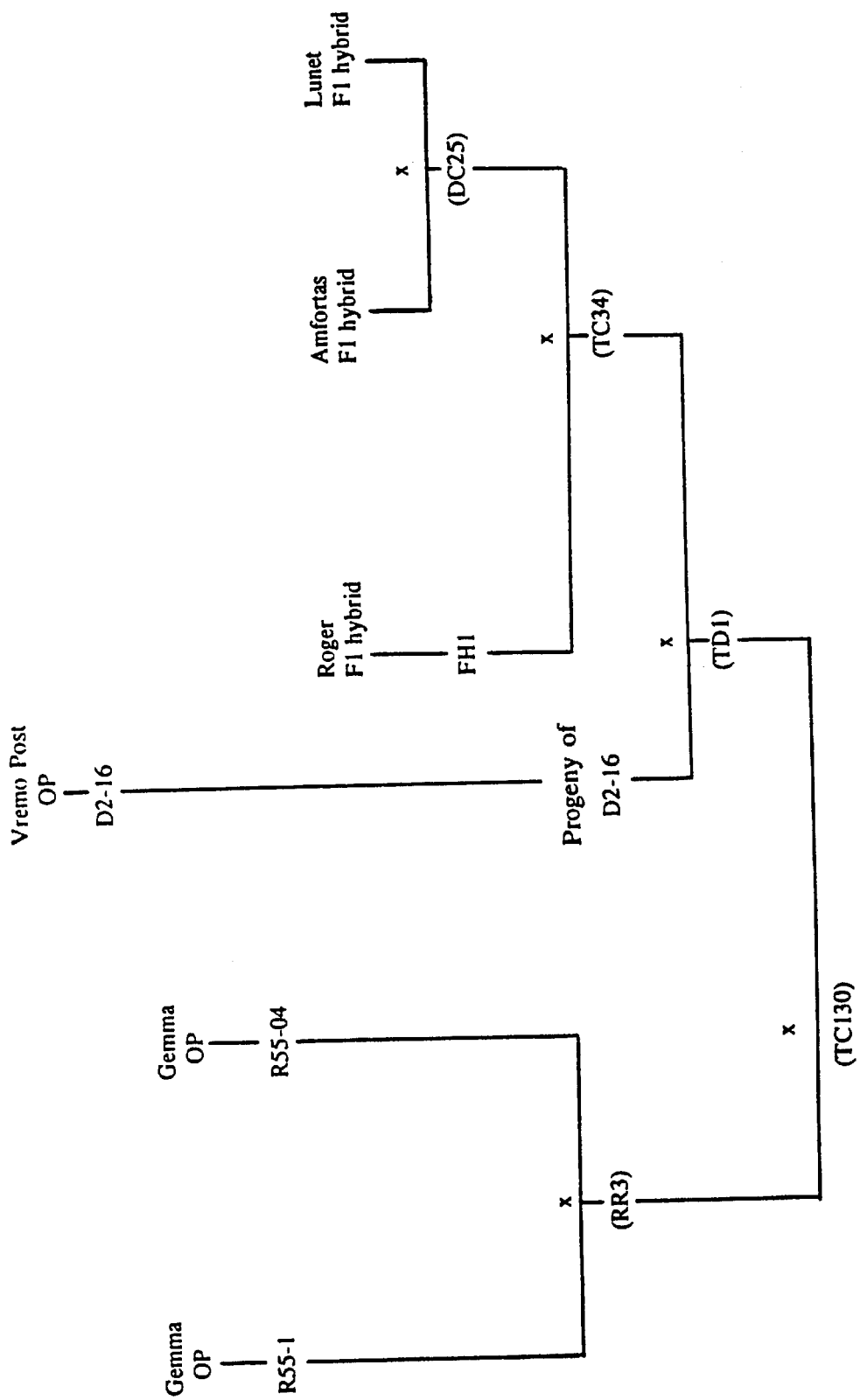

METHODS OF SELECTING PLANTS HAVING DELAYED OR INHIBITED RIPENING OR SENESCENCE

This application is a continuation of U.S. application Ser. No. 08/809,566, filed Mar. 25, 1997, now abandoned, which is a 371 application of PCT/EP95/03811, filed Sep. 25, 1995.

BACKGROUND OF THE INVENTION

1. Field of the Invention

The present invention relates to plants and plant parts exhibiting inhibited or delayed fruit ripening or tissue senescence. In particular, the invention relates to edible Brassica plants which display a delayed senescence, at least at room temperature.

2. Description of the Related Art

A problem faced by growers of plants destined for consumption is that harvesting of plants of a marketable age generally has to be performed over a time course of from about one to four weeks. If the time course for harvesting is too long, the edible portions of plants start visibly to deteriorate on the plant and become of limited commercial interest to the grower and/or retail outlet supplier. Retail outlets such as super-markets and the like try to extend the shelf life of plant parts by utilizing measures such as cooled shelving, water sprays, the use of plastic foil wrappings and gas manipulation. Although these work to a degree, there is still wastage of plant material, and hence loss of sales. Edible portions include those portions which are typically sold in the fresh produce shelves of super markets and the like or are sold to the canning and/or pickling industries.

In climacteric plants, including many members of the Brassica family, there is a rise in the rate of respiration and an associated production of ethylene at the onset of fruit ripening and the senescence of green tissues. In non-climacteric plants these changes are not observed. Ethylene is believed to trigger the ripening of fruits and senescence in leaves of climacteric plants and it has previously been shown that the exogenous addition of ethylene to such plants promotes these responses.

Cytokinins have a pronounced effect on the delay of senescence in fruits and other plant parts of climacteric plants. Cytokinins also play a role in cell division, the formation of lateral shoots, sprouts, flowers and fruits. Cytokinins are believed to be actively involved in the senescence process of plants when in the active free base and riboside configurations. Conversion of the active configuration of cytokinin into an inactive configuration in Brassica plants involves the addition of a sugar or amino acid moiety to the $N^{7,9}$-of the adenine ring of the cytokinin.

SUMMARY

The present invention provides inter alia, edible Brassica plants or edible parts thereof, exhibiting a modified ripening or senescence metabolism, the edible parts displaying substantially non-climacteric behavior.

According to the present invention there is provided a method of obtaining plants which exhibit delayed or inhibited fruit ripening and/or vegetable tissue senescence comprising:

(i) growing seedlings in the presence of an auxin polar transport inhibitor and selecting those seedlings the hypocotyledon of which grows at an acute angle of less than about 70° to the horizontal; or—

(ii) contacting the seeds of plants which have a low or reduced auxin polar transport with a conjugation inhibitory amount of an inhibitor of cytokinin-$N^{7,9}$glycosyl conjugation and selecting from the thus contacted seeds those which germinate.

A preferred embodiment of the method comprises performing steps (i) and/or (ii) indicated above to obtain selected plant products, selfing the thus obtained products and selecting by use of the said steps those that exhibit the traits of delayed or inhibited fruit ripening and/or vegetable tissue senescence, thereby to obtain a substantially homogeneous line with respect to these traits, and optionally crossing individuals of the said line, or the progeny thereof, with plants optionally exhibiting the said traits. It is particularly preferred that the said selfing and selection steps are repeated at least five times in order to obtain the homogeneous line.

It is preferred that the angle which the growing hypocotyledon makes with the horizontal is less than about 50°, still more preferred that the angle is less than about 25° and still more preferred that the angle is less than about 10°. Those plants obtained by the method of the invention which have the longest shelf life or delayed or inhibited senescence characteristics have hypocotyledons which grow substantially horizontally when seedlings thereof are subjected to inhibitors of polar auxin transport, even at very low concentrations, such as less than or equal to about 20 $\mu$M. Indeed a typical concentration of transport inhibitor used to select plants which have these desirable delayed senescence characteristics is about 1 to 10 $\mu$M, with 5 $\mu$M being substantially ideal for the selection of Brassicas, for example. It is particularly preferred that the transport inhibitor is chosen so that its effect on the seedling is substantially similar to that provided by about 5 to 10 $\mu$M HFCA (see below).

By "plants which have a low or reduced auxin polar transport" is meant plants in which the transport of auxin from its site of synthesis in the apical regions of the meristem to its site of utility in the known auxin sinks (such as leaves, for example) is at least 30% lower, more preferably at least 50% lower, still more preferably at least 80% lower, and still more preferably at least 90% lower than that in like plants which do not have a low or reduced auxin polar transport. One skilled in the art is aware of how auxin polar transport may be measured. One obvious way (as exemplified in Okada et al (1991) The Plant Cell Vol 3, pp. 677–694) to assess the auxin polar transport capacity of a plant is to add radiolabelled indole 3 acetic acid to one end of a cut inflorescence axis of plants suspected of having a low auxin transport and control plants known not to be deficient in this respect. Cut axes from the control plants are able to transport the radiolabelled auxin from one end to the other through the infloresence tissues in an inverted orientation, i.e. in a polar manner against gravity from the apical side to the basal side of the cut inflorescence. When incubated in a non-inverted orientation the cut inflorescence axis accumulates the radioactive auxin at the basal end of the tissues. Plants which have a low or reduced auxin polar transport are thus those which are substantially incapable of transporting auxin against gravity from the apical side to the basal side of, for example, a cut infloresecence.

"Delayed or inhibited fruit ripening and/or vegetable tissue senescence" provides for long shelf life, and these terms are more or less interchangeably used within the context of the present application. Delayed or inhibited fruit ripening or senescence (viz extended shelf life) can be determined in a manner known per se, for example, by visual comparison of plant parts after storage under standard conditions (time, temperature, humidity, sun-light etc.) with corresponding parts of like plants which do not constitute part of this invention (see below), or by determination of metabolic parameters of test plant parts with like parameters obtained from analysis of known plants of the same species. Examples of metabolic parameters suitable for indicating extended shelf life, include insensitivity to ethylene by plant parts which ripen or senescence.

By "polar transport inhibitor" is meant any compound or chemical which reduces or substantially prevents the transport of auxins from their site of synthesis in the apical meristem to their site of utility in the sink regions of the plant. The term thus includes compounds which bind auxins and as a consequence thereof prevent or otherwise inhibit auxin transport, as well as compounds which interfere with components of the auxin transport pathway. Known transport inhibitors include, amongst others, 9-hydroxyfluorene-9-carboxylic acid (HFCA), N-(1-naphthyl)phthalamic acid (NPA), silver thiosulfate (STS) and 2,3,5-tri-iodobenzoic acid (TIBA).

By "inhibitor of cytokinin-$N^{7,9}$-glycosyl conjugation" is meant any compound or other agent which prevents or reduces conjugation at the $N^{-7}$ or $N^{-9}$ position of cytokinins by amino acids or sugars, in particular glucose, xylulose or ribose. Such inhibitors thus include inhibitors of the known enzymnic systems (such as cytokinin-7-glucosyl transferase and $\beta$-(9-cytokini)alanine transferase) responsible for catalyzing such conjugations, thereby preventing or reducing cytokinin bio-inactivation. Known conjugation inhibitors include, amongst others, Papaverine, 6-benzylamino-2-(2-hydroxyethylamino)-9-methylpurine, 3-isobutyl-1-methylxanthine, theophylline, caffeine and theobromine etc, which may be administered at concentrations of between about 10 $\mu$M and 25 mM to the seeds of plants having low or reduced polar auxin transport so as to enable the selection from them, by virtue of their germination, of those that have delayed or inhibited ripening or senescence characteristics. In the case of Brussels sprouts, for example, seeds from plants which have a low or reduced auxin polar transport and which germinate in the presence of about 5 mM papaverine yield plants, at least the edible parts of which exhibit delayed tissue senescence. The conjugation and/or transport inhibitors are typically added to germination media. Media suitable for use in the method of the present invention, are those in which the conjugation or transport inhibitors dissolve easily and to which they do not bind. Typical examples of conventional growth media include agar and gelatin and the like, appropriately supplemented with plant hormones and nutrients.

The germination capacity of the seed in the presence of the conjugation inhibitor is determined under conventional germination conditions with respect to a particular plant species. Such germination conditions will of course vary to a lesser or greater extent from species to species but lie in general in the temperature range of from 10 to 20° C., preferably a temperature in the range of from 15 to 18° C. the seeds being kept in the dark. Clearly the seeds will need to be subjected to these conditions for a suitable time period, the minimum period during which the germination ability is determined is regarded as the time required for germination. Germination can be determined by the emergence of the radicle. A typical germination time for members of the B.oleracea lies in the range of 2 to 4 days, for example 3 days. Seeds of plants which have a low or reduced polar auxin transport and which germinate when contacted with a conjugation inhibitory amount of an inhibitor of cytokinin-$N^{7,9}$ glycosyl conjugation yield seedlings the development of which is essentially unaffected by the presence in a conventional growth medium of conjugation inhibitory amounts said inhibitor. Such seeds give rise to plants the edible parts of which exhibit an extended shelf life. By the term seedling "development" is meant hypocotyledon elongation and/or cotyledon stretching. Such development, which refers to initial seedling development, may be measured by placing the seeds to be tested on the media described above and incubating at the same or similar temperature as above described with respect to germination. Seedling development takes place, however, in the presence of light.

The invention also includes plants obtained by the method of the invention, in addition to plants which have a low or reduced polar auxin transport and delayed or inhibited fruit ripening or tissue senescence, (i) the hypocotyledon of the seedlings of which grows at an acute angle of less than about 70° to the horizontal when the seedlings are contacted with an inhibitor of polar auxin transport; and/or—(ii) the seeds of which germinate when contacted with a conjugation inhibitory amount of an inhibitor of cytokinin-$N^{7,9}$glycosyl conjugation. Specific examples of such plants include:

(i) *Brassica oleracea* L. *convar. gemmifera* DC (Brussels sprouts)

(ii) *Brassica oleracea* L. *convar. capitata* (L.) Alef. var. *alba* DC (white cabbage)

(iii) *Brassica oleracea* L. *convar. acephela* (DC.) Alef. var.*botrytis* L. (cauliflower)

(v) *Brassica oleracea* L. *convar. acephala* (DC.) Alef. var. *sabellica* L. (curly kale)

(vi) *Brassica oleracea* L *convar. capitata* (L.) Alef. var*.sabauda* L. (Savoy cabbage)

(vii) *Brassica oleracea* L. *convar. capitata* (L.) Alef. var. *rubra* DC (red cabbage)

(viii) *Brassica oleracea* L. *convar. acephala* (DC.) Alef. var. *gongylodes* (kohlrabi)

(ix) *Brassica oleracea* L. *convar. botrytis* (L.) Alef. var. *ithalica* (broccoli)

(x) *Brassica campestris* var *campestris* (Chinese cabbage).

(xi) *Lycopersicon esculentum*

(xii) *Capsicum annuum*

(xiii) *Cucumis melo*

When the term "edible" is associated with Brassica plants of the invention, the term means those plants usually grown for food or fodder, in particular Brassica plants fit for human consumption, including *B.oleracea* and *B.campestris*. When the term "edible" is associated with crops (xi)–(xiii) above, the term means fruits. Typical examples of edible plants of the invention include *Brassica oleracea* plants such as examples (i) to (ix); and *Brassica campestris* such as example (x) above. Particularly preferred Brassica plants of the invention include green (savoy) cabbage, Brussels sprouts, broccoli and Chinese cabbage as per the above. It is to be understood that the Brassica types referred to in (i) to (x) describe Brassica types in a generic sense. For example *Brassica oleracea* L. *convar. botrytis* (L.) Alef. var. *ithalica* describes broccoli plants whether they be purple sprouting, green or any other suitable broccoli type.

It will be appreciated that in respect of the plants of the invention the delayed or inhibited fruit ripening or tissue senescence traits will preferably be stably inherited in a Mendelian manner. The invention also includes the progeny of the said plants, and/or the seeds of such plants or such progeny. It is to be understood that the said traits are inheritable in the said progeny and seeds, and that their transfer to the progeny or seeds may involve crossing with plants from the same sub-species, back-crossing and the like, as is well known to the skilled plant breeder.

The invention still further includes edible parts of the said plants and progeny, which parts exhibit delayed or inhibited senescence or ripening when subjected to amounts of ethylene which cause senescence or ripening in plants (i) the hypocotyledon of the seedlings of which grows at an acute angle of greater than about 70° to the horizontal when the seedlings are contacted with an inhibitor of polar auxin transport; and/or—(ii) the seeds of which do not germinate when contacted with a conjugation inhibitory amount of an inhibitor of cytokinin-$N^{7,9}$glycosyl conjugation. It is particularly preferred that the edible parts are derived from *Brassica oleracea, Brassica campestris, Lycopersicon esculentum, Capsicum annuum* or *Cucumis melo* plants. Ripening or senescence-inducing amounts of ethylene may be established by standard tests. Said amounts will depend, inter alia, on the identity of the individual plant species. Brussels sprouts buttons obtained from plants of the invention typically show no visible symptoms of deterioration over a period of time from about 2 days to about 14 days or more when placed in the presence of amounts of ethylene which cause senescence in commercially available sprouts.

Edible parts of plants of the invention, having an extended shelf life when stored in the range of from 15 to 25° C. show substantially no visible signs of deterioration due to overripening or advanced senescence during the time periods indicated below.

Edible parts derived from plants of the invention typically have a sufficiently delayed tissue senescence or fruit ripening trait to provide for an extended shelf-life when they are stored at a temperature in the range of from 15 to 25° C., compared to that of parts of like plants of the same species lacking the trait provided by the invention. For example, the average shelf-life for broccoli florets and Brussels sprouts buttons derived from known plants when stored in the temperature range of from 15 to 25° C. is of the order about 2 and 5 days respectively. In contrast, Brussels sprouts buttons derived from plants of the invention have a shelf-life of at least 3 to 6 days or more, under similar conditions of storage. Preferably broccoli florets of the invention have a shelf life in the range of from 3 to 7 days when stored in the temperature range of from 15 to 25° C. Preferably Brussels sprouts buttons of the invention have a shelf life in the range of from 6 to 14 days when stored in the temperature range of from 15 to 25° C. More preferably Brussels sprouts buttons of the invention have a shelf life in the. range of from 6 to 20 days when stored in the temperature range of from 15 to 25° C. Typically, such Brassica plant parts do not require the use of water sprays and cooled shelves and the like to keep them fresh-looking, although such means may be used further to extend the shelf-life of such plant parts. Examples of edible parts of the plants of the invention include tomato and pepper fruits, melons and various edible parts of Brassica species, for example, Brussels sprouts buttons, broccoli heads or florets and/or shoots, cauliflower heads and/or florets, cauliflower leaves, cabbage heads and Chinese cabbage heads etc.

The invention still further includes the use in the manufacture of plant varieties of totipotent cells growing in culture, seeds, leaf, stem, roots, shoots and the like, protoplasts, somatic embryos, anthers, stamens, and petioles, derived from the plants or seeds of the invention Seeds of the established plant line designated herein as TC130 were deposited on Jul. 12, 1994 with the National Collections of Industrial and Marine Bacteria Ltd., International Depository Authority. St Machar Drive, Aberdeen, Scotland, and received the designation number NCIMB 40673. Where permissible under the corresponding patent law regulations (Rule 28EPC, for example), the availability of this deposit to third parties is restricted to an expert intermediary either nominated by the President of the appropriate Patent Office or by the third party provided that the third party nomination is approved by the applicant.

The invention will be further apparent from the following specific description taken in conjunction with the associated drawing which illustrates a breeding scheme for obtaining a Brussels sprouts line exhibiting a delayed tissue senescence characteristic according to the invention.

DETAILED DESCRIPTION OF THE INVENTION

Production of the Brussels Sprouts Line TC 130

Progress in the selection of plants the edible parts of which exhibit extended shelf life is related to the genetic background of the plants used in the various combinations and selfings. During the selection process which yielded TC130, attention has been paid to the following traits: standing ability, lateness and button quality. These traits appear at least to some extent to be linked with low or reduced auxin polar transport. Brussels sprouts open pollinated variety Gemma, (Groot Sloot B. V.), is selfed 1×, and a resulting plant R55-1 (in-house designation), displaying inter alia good standing and lateness is selected for further selfing, and is selfed 6×. A further plant R55-04 (in-house designation), displaying lateness, winter hardiness, and good standing ability is selected (also obtained from a 1× selfing from Gemma), and is selfed 6×. The resulting populations of R55-1 and R55-04 are crossed forming a population, designated in FIG. 1 as RR3.

A further Brussels sprouts F1 hybrid, Roger (S&G Seeds), is selfed 6× and a population of plants, designated FH1 is obtained.

Brussels sprouts F1 hybrid varieties Amfortas (S&G Seeds) and Lunet (Royal Sluis) are crossed providing an inbred line of plants designated as DC25, displaying inter alia good standing ability and small sprout buttons. Plant line DC25 and FH1 are crossed and selected plants displaying desirable characteristics are then selfed 6×, forming plant population TC34 displaying inter alia lateness and small sprout buttons.

Commercial open pollinated variety Vremo Post, displaying inter alia good yield and good standing ability is selfed resulting in a population of plants designated as D2. Plant D2-16 is selected on the basis of good yield, earliness, and good standing ability and is selfed 6×.

The selfed progeny of D2-16 is then crossed with TC34, forming plant population TD, from which plant TD1 is selected on the basis of good yield, earliness, and good standing ability for crossing with plant RR3, forming a population of plants TC, from which plant TC130 is selected for repeated selfings (6×), resulting in plant line TC130. Plant line TC 130 is found to display a delay in the onset of senescence at a temperature in the range of from 15 to 25° C., compared to plants not comprising the modified ripening trait of this invention. Furthermore it displays good standing ability and good shelf life or delayed senescence characteristics, for which traits it is homozygous.

Obtention of Broccoli Plants Displaying Inter Alia Characteristics of Delayed Senescence at Room Temperature TC130, obtained as indicated above, is crossed with a broccoli line S&G#, displaying conventional shelf life characteristics. The resulting F1 hybrid displays a delay in onset of senescence in the floret (see Table 5).

Shelf-life of Brussels Sprouts

The shelf life of five different types of Brussels sprouts is determined as described below. The sprouts to be tested are harvested at the same time, thus the time elapsed since harvesting is the same for each type of sprout.

TC130, Spr 110 (hybrid of TC130 and a parental line not having extended shelf life) and the commercially available varieties Phylemon, Corinth and Kundry (S&G Seeds B.V.) are tested. Kundry is a conventional cultivar known to have particularly good shelf life by the standards of the prior art. The sprouts are stored in transparent plastic bags (100 g/bag) at 20° C. under natural light conditions.

The shelf life is judged according to the number of yellow leaves each type produces as a function of time. Shelf-life is expressed on a scale of between 1 (no shelf-life) and 9 (long shelf-life). Sprouts have on average 6 wrapper leaves. The number of yellow leaves is the average value of 10 buttons. The results are given in Table 1 below, where it can be clearly seen that TC130 and Spr110 have extended shelf life compared to conventional cultivars. In comparison with Kundry in which all the leaves are yellow by day 6, it is clear that the plants of the present invention, have far superior shelf life.

TABLE 1

| Cultivar/line | shelf-life | Number of yellow wrapper leaves | | | | |
| --- | --- | --- | --- | --- | --- | --- |
| | | harvest | 2 days | 3 days | 6 days | 14 days |
| TC130 | 9 | 0 | 0 | 0 | 0 | 2 |
| Spr 110 | 9 | 0 | 0 | 0 | 2 | 2 |
| Phylemon | 5 | 0 | 3.3 | 5.4 | 6 | rotten |
| Corinth | 1 | 0 | 4 | 6 | 6 | rotten |
| Kundry | 7 | 0 | 0.4 | 0.4 | 6 | rotten |

Determination of Ethylene Production

Ethylene production of the five types of Brussels sprouts indicated in Table 2, is measured over the course of 3 days. Thus, ethylene concentration is determined in the headspace of closed jars using gas chromatography. The concentration of ethylene is expressed as $\mu l.1^{-1} gram^{-1}$ sprout mass. Shelf-life is assessed as indicated above.

It can be seen from Table 2 that by day 3, the concentration of ethylene above sprouts from TC130 and Spr110 (both of which display extended shelf life) is relatively low compared to the that generated by conventional sprout types.

TABLE 2

| Cultivar/line | shelf life | Ethylene concentration ($\mu l.1^{-1}$ gram$^{-1}$) | | | |
| --- | --- | --- | --- | --- | --- |
| | | harvest | 1 day | 2 days | 3 days |
| TC130 | 9 | 0 | 1.7 | 3.4 | 2.8 |
| Spr 110 | 9 | 0 | 1.2 | 2.7 | 4.7 |
| Phylemon | 5 | 0 | 2.2 | 4.5 | 7.4 |
| Corinth | 1 | 0 | 3.3 | 4.7 | 10.1 |
| Kundry | 7 | 0 | 4.1 | 6.5 | 10.4 |

Effect of Added Etheylene on the Senescence of Brussels Sprouts

Ethylene is added to TC130, and Spr110 in the form of a water spray containing 200 ppm Ethephon in the form of Ethrel A™ (Luxan, The Netherlands). 200 ppm Ethephon corresponds to about 40 ppm of bound ethylene. A control in the form of a water spray without Ethephon is carried out to measure senescence in the absence of Ethephon. Sprouts of commercially available varieties Corinth, Phylemon and Ajax are also used as a control.

Table 3 shows that sprouts from the line TC130 and the cultivar Spr110 do not start to turn yellow up to 7 days after spraying with water or 200 ppm Ethephon. Water-sprayed sprouts from the cultivars Corinth, Phylemon and Ajax start to turn yellow quickly and are totally yellow after 7 days. In the table, 200 ppm denotes treatment with Ethephon at a concentration of 200 ppm.

TABLE 3

| Cultivar | Treatment | Number yellow leaves | | | |
| --- | --- | --- | --- | --- | --- |
| | | harvest | day 1 | day 2 | day 7 |
| TC130 | water | 0 | 0 | 0 | 0 |
| | 200 ppm | 0 | 0 | 0.5 | 0.5 |
| Spr 110 | water | 0 | 0 | 0 | 0 |
| | 200 ppm | 0 | 0 | 0 | 0 |
| Corinth | water | 0 | 1.1 | 1.3 | 6 |
| Phylemon | water | 0 | 1.6 | 4.1 | 6 |
| Ajax | water | 0 | 3.7 | 5.8 | 6 |

As can be seen from Table 4 below, the ethylene concentration (determined as indicated above) in the headspace above the Ethephon sprayed sprouts of TC130 and Spr 110 after day 2, is higher than the ethylene concentration above water sprayed Corinth and Phylemon sprouts. Despite a high ethylene concentration in the headspace above Ethephon sprayed sprouts from TC130 and Spr110, no senescence is observed 7 days after spraying.

TABLE 4

| Cultivar | Treatment | Ethylene concentration ($\mu l.1^{-1}.gram^{-1}$) in the Headspace | | |
| --- | --- | --- | --- | --- |
| | | harvest | day 1 | day 2 |
| TC130 | water | 0 | 2 | 3 |
| | 200 ppm | 0 | 114 | 91 |
| Spr 110 | water | 0 | 1 | 3 |
| | 200 ppm | 0 | 45 | 64 |
| Corinth | water | 0 | 3.3 | 4.7 |
| Phylemon | water | 0 | 20 | 31 |
| Ajax | water | 0 | 108 | 255 |

The ethylene concentration in the headspace is corrected for the sprout mass in the jars and expressed as $\mu l.1^{-1} gram^{-1}$. In the Table, 200 ppm denotes 200 ppm Ethephon.

From the results summarized in Tables 2–4 it can be seen that although the production of ethylene by plants of the invention is relatively low compared to conventional plants (see Table 2), this is not the factor responsible for their extended shelf life i.e. delayed or inhibited vegetable tissue senescence, as even in the presence of high concentrations of ethylene, senescence does not occur or is substantially delayed in these plants. It may be that the sprouts of the invention have lost the capacity to exhibit the climacteric response displayed by commercially available prior art sprouts, namely that of displaying an onset of senescence in the presence of ethylene.

Extended Shelf-life in Broccoli Florets Heterozygous for the Sprout Shelf-life Trait The Broccoli line S&G# (which displays conventional short shelf life) is crossed with respectively sprout line TC25, which also displays short shelf-life and sprout line TC130 which has extended shelf life characteristics. The floret quality of the sprout-broccoli combinations is comparable with broccoli florets. Florets from S&G# plants, plants from an S&G#×TC25 cross and plants from an S&G#×TC130 cross are evaluated for shelf life by observing the rate of yellowing of the florets during storage. The florets are initially sprayed with water or 200 ppm Ethephon as described above. Table 5 shows that the florets of the S&G#×TC130 cross start to turn yellow significantly more slowly than their counterparts from the S&G# and S&G#×TC25 cross after spraying with water. Florets from the S&G#×TC130 cross turn yellow 7 days after treatment with Ethephon as mentioned above, while florets from S&G# and S&G#×TC25 cross are yellow 2 days after the same treatment. Thus Florets from the S&G#×TC130 cross have an extended shelf life of about 3 days at 20° C. when sprayed with water, in comparison to those of S&G# and the S&G#×TC25 cross, and of about 2 days after a treatment with 200 ppm Ethephon as mentioned above.

TABLE 5

The rate of yellowing is scored according to the following visual scale: green - light green - green/yellow - yellow/green - yellow - brown.

| | | Color of broccoli | | | |
|---|---|---|---|---|---|
| Cultivar | Treatment | harvest | day 2 | day 3 | day 7 |
| S&G# | water | green | green | green/yellow | yellow |
| | 200 ppm | green | yellow | yellow | brown |
| S&G#xTC25 | water | green | green | green/yellow | yellow |
| | 200 ppm | green | yellow | yellow | brown |
| S&G#xTC130 | water | green | green | light/green | light/green |
| | 200 ppm | green | green | green/yellow | yellow |

Storage Capability and Shelf-life of Brussels Sprouts

Brussels sprout cultivars are evaluated for both storeability and shelf-life. When the sprouts are "stored" they are generally subjected to conditions specifically adapted to prevent senescence or vegetable ripening. Shelf-conditions are generally more adverse in respect of this prevention of senescence or ripening, and typically include increased illumination, lower humidity and/or higher temperature. Table 6 shows the color of sprouts from a selection of various cultivars before, during and after a prolonged storage period. Fresh, green sprouts are picked and sorted according to size. Thus Category A sprouts having a diameter of 20–30 mm are chosen. The sorting is complete 24 h after harvest. The sorted sprouts are stored for an initial 11 day storage period in a dark air conditioned room at 4° C., followed by an 13 day shelf-life period at 15° C. Table 6 shows that cultivars obtained via a cross involving line TC130 (hereinafter referred to as TC130-type cultivars) stay green up to 24 days after picking. Thus, it is clear that sprouts from TC130 and TC130-type cultivars exhibit long shelf-life, in comparison with prior art cultivars. Thus, for example, Corinth and Content begin to turn yellow during the sorting process (day 0 in Table 6), become more yellow within the storage period (day 5 in Table 6) and turn totally yellow within the shelf life period (day 24 in Table 6). In Table 6, shelf-life and store-ability are scored on a 1–9 category scale (1=totally yellow, 9=fresh green).

TABLE 6

| | Color | | |
|---|---|---|---|
| Cultivar | day 0 | day 5 | day 24 |
| TC130 × DC127 | 9 | 8 | 8 |
| TC130 × DC130 | 9 | 9 | 8 |
| Adonis | 8 | 7 | 5 |
| Ajax | 8 | 6 | 3 |
| Philemon | 6 | 5 | 2 |
| Content | 6 | 5 | 1 |
| Lauris | 6 | 4 | 1 |
| Asgard | 6 | 4 | 1 |
| Corinth | 6 | 5 | 1 |

Evaluation of Shelf-life or Brussels Sprouts Under Standard Conditions

Parental lines and cultivars are evaluated. The shelf-life of the various lines and cultivars is presented in Table 7. Fresh, green sprouts are picked, sorted (as above) and thereafter stored for a 5 day period at 20° C. under natural light conditions. TC130 and TC130-type cultivars (TC130×DC69 and TC130×TC127) stay green until sorted, while lines and cultivars such as Content and DC94 quickly start to turn yellow. TC130 and TC130-type cultivars clearly have a extended shelf-life relative to other lines and cultivars when stored under standard conditions (high temperature in the presence of light) described. The scoring in Table 7 is the same as that indicated above for Table 6.

TABLE 7

| | Color | |
|---|---|---|
| Line/Cultivar | after sorting | 5 days |
| TC130 | 8 | 6 |
| DC69 | 7 | 2 |
| TC127 | 8 | 4 |
| TC130 × DC69 | 9 | 6 |
| TC130 × TC127 | 8 | 6 |
| Icarus | 6 | 1 |
| Content | 3 | 1 |
| Ajax | 8 | 1 |
| Adonis | 8 | 3 |

Ability of Seeds From Sprout Lines and Cultivars to Germinate and Develop in the Presence of Papaverine Seeds are placed on agar in the dark for 5 days and subsequently exposed to light (16 h TL33 light, 8 h darkness, at 22° C.). Whether germination has occurred or not is determined on removing the seeds from the dark. Seedling development is scored on day 18 using parameters such as cotyledon stretching and hypocotyledon elongation. The results depicted in Table 8 demonstrate the effect of 5 mM Papaverine on a number of lines (RR3, TC17 and TC22) and hybrid cultivars. The plants tested are divided into two classes: Class 1, which do not display an extended shelf life; and Class 2 which do display an extended shelf life. Class 1 comprises RR3, TC17, TC22, Corinth, Phylemon, Ariston, and Ajax. Class 2 comprises Spr105, 108, 114, 66, 104, 115 and TC130. All of the Spr hybrids have TC130 as a parent (homozygous for extended shelf life) and a parent not displaying extended shelf life. Thus Spr105 is a hybrid of TC130 and DC69 (conventional shelf life).

TABLE 8

| CLASS | CULTIVAR/ LINE | GERM- INATION | HYPO- COTYLEDON ELONGATION | COTYLEDON STRETCHING |
|---|---|---|---|---|
| 1 | RR3 | − | − | − |
| 1 | TC17 | − | − | − |
| 1 | TC22 | − | − | − |
| 1 | Corinth | − | − | − |
| 1 | Phylemon | − | − | − |
| 1 | Ajax | − | − | − |
| 1 | Ariston | − | − | − |
| 2 | Spr105 | + | + | + |
| 2 | Spr108 | + | + | + |
| 2 | Spr114 | + | + | + |
| 2 | Spr66 | + | + | + |
| 2 | Spr104 | + | + | + |
| 2 | Spr115 | + | + | + |
| 2 | TC130 | + | + | + |

Normal = +
Total inhibition = −

Class 1 plants fail to germinate, and neither develop hypocotyledons nor cotyledons in the presence of Papaverine, whereas Class 2 plants, germinate and develop hypocotyledons and cotyledons in the presence of Papaverine. It is also clear that seedling development in Class 2 plants is unaffected by 5 mM Papaverine, whereas in Class 1 plants neither hypocotyledon elongation nor cotyledon stretching occurs.

Evaluation of TC130 for Auxin Response

The polar auxin transport of the Brassica line TC130 and other cultivars is evaluated. Polar auxin transport is inhibited by application of HFCA (9-hydroxy-9-fluorene-carboxylic acid) to the medium in which the sprout seeds are germinated. When sprout seeds are subjected to HFCA during the germination process on agar, the resulting seedlings loose their gravitropic response in the case the auxin polar transport is inhibited. The angle between the hypocotyledon and the surface in the presence of HFCA is a measure of the capacity of the seedling to transport auxins from their site of synthesis to the sites of their action (consumption). Seedlings the hypocotyledons of which grow at an angle of 90° to the horizontal when in the presence of an auxin polar transport inhibitor have a relatively high polar auxin transport capacity, whereas the hypocotyledon of like seedlings, which grow at an angle of about 0° to the horizontal have a very low auxin polar transport. Table 9 shows the angle between hypocotyledon and (horizontal) surface for a selection of sprout lines and cultivars.

TABLE 9

Influence of HFCA on polar auxin transport of Brussels sprout lines and cultivars (determined as hypocotyledon-surface angle).

| Cultivar/line | Angle (°) | Extended shelf-life |
|---|---|---|
| TC130 | 20 | yes |
| RR3 | 90 | no |
| DC69 | 90 | no |
| Corinth | 90 | no |
| Phylemon | 90 | no |
| Ajax | 90 | no |
| Kundry | 90 | no |
| Spr 105 (TC130) | 20 | yes |
| Spr 111 (TC130) | 20 | yes |
| Spr 108 (TC130) | 20 | yes |

Senescence of Young Leaves from TC130 Generations and Non-LSL Cultivars After Treatments With 100 ppm Ethrel The third true leaf from young Brussels sprout plants, having 6 true leaves, is dissected and transferred with its petiole into a basal nutrient solution with and without 100 ppm Ethrel. The rate of yellowing with respect to time is monitored, and the results are presented in Table 10.

TABLE 10 Rate of yellowing of young leaves of Brussels sprouts during a treatment with 100 ppm Ethrel via the petiole. Yellowing is scored on a category scale in ascending order: green, green/yellow, yellow/green, yellow, yellow/brown and brown/dry. +E=treatment with 100 ppm of Ethrel. −E=treatment with water.

| Cultivar/ line | Exp. | Colour day 5 −E | day 5 +E | day 6 −E | day 6 +E | day 7 −E | day 7 +E |
|---|---|---|---|---|---|---|---|
| Ajax | 1 | green | yellow | green | yellow/brown | green | brown/dry |
|  | 2 | green | yellow | green | yellow/brown | green | brown/dry |
| Corinth | 1 | green | yellow/green | green | yellow | green | yellow/brown |
|  | 2 | green | yellow/green | green | yellow | green | yellow/brown |
| TC 130 | 1 | green | green | green | green | green | green/yellow |
|  | 2 | green | green | green | green | green | green/yellow |

From the table it is clear that the rate of yellowing is significantly slower in leaves from the LSL-line TC130. A delay of about two days in the rate of yellowing is observed in TC130 leaves in comparison to leaves from non-LSL cultivars Ajax and Corinth. A treatment with 100 ppm Ethrel discriminates (optimally at day 7) for shelf-life on leaves at the young plant stage.

Whilst the invention has been particularly described by way of the production of Brassicas having delayed tissue senescence or ripening, the skilled man will appreciate that the method of the invention may be applied to the obtention of any suitable plants which exhibit such characteristics. In particular tomatoes, melons and peppers having long shelf life characteristics may be selected by growing seedlings thereof in the presence of auxin polar transport inhibitors and selecting those the hypocotyledons of which do not grow substantially vertically, or by contacting the seeds thereof with cytokinin glycosyl conjugation inhibitors and selecting those that germinate. Other plants which may likewise be selected are included within the group consisting of field crops, vegetables and fruits including tomato, pepper, melon, lettuce, cauliflower, broccoli, cabbage, brussels sprout, sugar beet, corn, sweetcorn, onion, carrot, leek, cucumber, tobacco, alfalfa, aubergine, beet, broad bean, celery, chicory, cow pea, endive, gourd, groundnut, papaya, pea, peanut, pineapple, potato, safflower, snap bean, soybean, spinach, squashes, sunflower, sorghum, watermelon and the like; and ornamental crops including impatiens, begonia, petunia, pelargonium, viola, cyclamen, verbena, vinca, tagetes, primula, saint paulia, ageratum, amaranthus, anthirrhinum, aquilegia, chrysanthemum, cineraria, clover, cosmo, cowpea, dahlia, datura, delphinium, gerbera, gladiolus, gloxinia, hippeastrum, mesembryanthemum, salpiglossis, zinnia, and the like.

Moreover, the plants which exhibit delayed or inhibited fruit ripening and/or vegetable tissue senescence and which are selected or are obtainable by the method of the invention may be subjected to a repeated process of selfing and selection thereby to produce a homogeneous plant line with respect to these traits. The resulting such plants (or the progeny thereof) may be crossed with plants which optionally exhibit such traits to produce hybrids, for example. In a particular embodiment of the invention, the non-inventive plants involved in the cross may exhibit delayed or inhibited ripening and/or vegetable tissue senescence as a consequence of their being transformed so that the activities of the enzymes involved in ripening or senescence are inhibited or substantially diminished, perhaps by sense co-suppression or antisense inhibition of polygalacturonase, for example.

What is claimed is:

1. Seed of Brassica inbred line TC130, seed of said Brassica inbred line having been deposited under designation number NCIMB 40673.

2. A Brassica plant, or parts thereof, of inbred line TC130, seed of said Brassica inbred line having been deposited under designation number NCIMB 40673.

3. Pollen of the plant of claim 2.

4. An ovule of the plant of claim 2.

5. A Brassica plant having all of the physiological and morphological characteristics of the plant of claim 2.

6. A F.sub.1 hybrid seed produced by crossing the Brassica plant of claim 2 with another Brassica plant.

7. A F.sub.1 hybrid plant, or parts thereof, grown from the seed of claim 6.

* * * * *